United States Patent
Wilson

[11] Patent Number: 6,074,461
[45] Date of Patent: Jun. 13, 2000

[54] CHROMATOGRAPH HAVING A GAS RECYCLING SYSTEM

[75] Inventor: William H. Wilson, Newark, Del.

[73] Assignee: Hewlett-Packard Company, Palo Alto, Calif.

[21] Appl. No.: 09/126,531

[22] Filed: Jul. 30, 1998

[51] Int. Cl.[7] .................................................. B01D 15/08
[52] U.S. Cl. ............................... 96/102; 96/4; 96/103; 96/130
[58] Field of Search .................................. 95/53, 55, 56, 95/82–89, 127; 96/4, 101–108, 130

[56] References Cited

U.S. PATENT DOCUMENTS

| | | | |
|---|---|---|---|
| Re. 35,725 | 2/1998 | Briesacher et al. ................. | 96/108 X |
| 3,172,741 | 3/1965 | Jolley ................................. | 95/53 |
| 3,256,675 | 6/1966 | Robb .................................. | 95/53 |
| 3,357,157 | 12/1967 | O'Donnell ......................... | 95/84 |
| 3,400,514 | 9/1968 | Noda .................................. | 96/106 X |
| 3,455,817 | 7/1969 | Modell .............................. | 95/82 X |
| 3,589,171 | 6/1971 | Haley ................................. | 95/56 X |
| 3,624,986 | 12/1971 | Shoemake ......................... | 96/102 X |
| 3,638,396 | 2/1972 | Lovelock .......................... | 95/56 |
| 3,638,397 | 2/1972 | Charlton ............................ | 95/56 |
| 3,712,028 | 1/1973 | Deans ................................ | 95/82 |
| 3,713,271 | 1/1973 | Franz et al. ....................... | 95/53 |
| 3,818,679 | 6/1974 | Klass et al. ........................ | 95/280 |
| 3,971,768 | 7/1976 | Peters et al. ....................... | 526/68 |
| 4,230,464 | 10/1980 | Bonmati et al. ................... | 95/22 |
| 4,238,204 | 12/1980 | Perry ................................. | 95/56 X |
| 4,472,176 | 9/1984 | Rubin ................................ | 95/56 |
| 4,537,759 | 8/1985 | Walker et al. ..................... | 95/82 X |
| 4,762,535 | 8/1988 | Pez et al. ........................... | 95/44 |
| 4,994,096 | 2/1991 | Klein et al. ....................... | 95/82 X |
| 5,108,466 | 4/1992 | Klein et al. ....................... | 95/82 X |
| 5,205,841 | 4/1993 | Vaiman ............................. | 95/56 X |
| 5,205,843 | 4/1993 | Kaschemekat et al. ........... | 95/39 |
| 5,567,227 | 10/1996 | Henderson ........................ | 95/82 X |
| 5,622,682 | 4/1997 | Tom .................................. | 423/230 |
| 5,698,011 | 12/1997 | Chung et al. ...................... | 95/45 |
| 5,895,519 | 4/1999 | Lorimer ............................. | 96/108 X |

Primary Examiner—Robert Spitzer

[57] ABSTRACT

A chromatograph includes an inlet for receiving a sample and a pressurized carrier fluid flow and in response providing a sample/fluid mixture; a separation column located in a temperature-controlled zone for receiving the sample/fluid mixture and for providing a column effluent stream; a detector for receiving the effluent stream and for providing a detector output stream; and a gas recycling system for receiving the detector output stream, and optionally a split flow and a septum purge line flow, and for providing therefrom a recycled carrier gas stream suitable for reuse as the pressurized carrier fluid flow.

12 Claims, 3 Drawing Sheets

CHROMATOGRAPH HAVING A GAS RECYCLING SYSTEM

CROSS REFERENCE TO RELATED APPLICATION

This application is related to commonly-assigned U.S. patent application Ser. No. 09/126,530 filed on even date herewith, in the name of William H. Wilson, and entitled "CHROMATOGRAPH HAVING A GAS STORAGE SYSTEM".

FIELD OF THE INVENTION

The present invention relates to methods and apparatus for use in analytical instrumentation for the detection of an analyte in a carrier gas, wherein the instrumentation includes a system for recycling of the carrier gas.

BACKGROUND OF THE INVENTION

A simplified schematic view of a conventional chromatograph 100 is shown in FIG. 1. The illustrated chromatograph 100 is representative of a Hewlett-Packard 6890 Gas Chromatograph. Analytical instruments such as the gas chromatograph 100 are known for use in determining the chemical composition of a sample which is typically injected at an inlet 112 into a carrier gas stream provided by a carrier gas source 111 through a manifold 113. A fluid mixture of the sample and the carrier gas is directed through a separation column 114 located within an oven 116 and exposed to a controlled temperature environment provided by a heater 118. The separation column 114 includes a stationary phase coating on the interior of the column. The interaction of the constituent compounds in the sample with the stationary phase cause differing chemical compounds in the sample to travel through the separation column at different rates and to leave the separation column at different times. The presence of compounds in the column effluent gas is sensed by a detector 124. A detector output signal is provided to a controller 126 and a computer 122 on signal lines 128,130. The compound of interest is typically called an analyte.

A significant shortcoming in the conventional gas chromatograph is due to the loss of one or more gas streams that are typically vented to the atmosphere from the inlet 112 or the detector 124. The majority of the composition of such streams is carrier gas; for example, if the inlet 112 is constructed as a split/splitless inlet, much of the carrier gas employed by the chromatograph 100 is vented away from the inlet 112. Accordingly, a column with a 1 ml/min flow rate and a split ratio of 100:1 will vent 100 times the amount of gas actually required to carry a sample through the column 114 for an analysis. Six liters of carrier gas at inlet pressure are typically lost to the surrounding environment during one hour of analysis. However, if the carrier gas were to be conserved, such a volume of gas could easily supply a column flow for many more hours of continuous operation.

The high rate of consumption of carrier gas observed in the conventional apparatus is one of the major factors that have inhibited the development of portable instrumentation, and has also limited the deployment of most bench top (i.e., non-portable) chromatographs in underdeveloped areas of the world where cylinders of carrier gas are in short supply.

There thus exists a need for analytical instrumentation that employs a carrier gas recycling system wherein, among other factors, the flow of the carrier fluid is conserved and reused to an extent satisfactory for most analytical applications.

SUMMARY OF THE INVENTION

The advantages of the invention are achieved in a preferred embodiment of an analytical instrument, preferably provided in the form of a chromatograph, wherein an integral gas recycling system receives the gas streams that would be otherwise be vented to the atmosphere in a conventional apparatus, purifies the received gas streams in order to remove the residual impurities, pressurizes the purified gas, and returns the pressurized gas to a reservoir of carrier gas for subsequent reuse.

The preferred embodiment includes an inlet for receiving a sample and a pressurized stream of carrier gas supplied from a carrier gas reservoir, and in response, providing a sample/fluid mixture and (in some embodiments that operate a split/splitless inlet) an inlet output stream in the form of a combination of a split flow and a purge flow; a separation column located in a temperature-controlled compartment for receiving the sample/fluid mixture and for providing a column effluent stream; a detector for receiving the column effluent stream and providing in response a detector output signal and a detector output stream; a gas recycling system for receiving the detector output stream and, in certain embodiments, the inlet output stream, for purification and pressurization of the received streams and for providing a recycled gas stream to the carrier gas reservoir.

The preferred embodiment may optionally include a control system including a computer for sensing the volumetric flow rate of the fluid mixture entering the column and for generating a respective flow rate signal and for sensing the column input pressure and generating a respective input pressure signal, and an electronic pneumatic controller including means for receiving the flow rate signal and input pressure signal, for controlling a valve operable and to control the input pressure and the volumetric flow rate of the carrier fluid provided to the inlet. The detector generates a detector output signal, whereby one or more characteristics of the effluent stream that are related to the analyte of interest may be represented by the output signal.

In a first aspect of the invention, some or all of the input and output pressures, and the carrier fluid volumetric flow rate, may be controlled by the electronic pressure controller, which thereby offers control of any unwanted flow rate variation in the pressurized carrier gas stream that is output from the gas recycling system described herein.

In another aspect of the invention, the chromatograph may be provided in the form of a compact planar assembly wherein some or all of the fluid handling functions related to the aforementioned gas streams are effected via fluid-handling functional devices mounted on a planar manifold assembly. The planar manifold assembly includes one or more fluid-handling functional devices attached to a planar manifold. The planar manifold includes internal etched channels capable of bearing one or more of the aforementioned fluid streams. Certain ones of the fluid-handling functional devices may be miniaturized and surface mounted to the planar manifold.

In another aspect of the invention, the gas recycling system may be provided in the form of a gas purification system and a gas pumping system located in a module on the planar manifold assembly, whereby the gas recycling system is in fluid communication with internal channels which convey the column effluent fluid stream and the inlet output stream, such that the gas recycling system is pneumatically integrated with the planar manifold assembly.

In another aspect of the invention, the separation column may be integrated within the planar manifold as an etched serpentine channel.

DETAILED DESCRIPTION OF THE PREFERRED EMBODIMENT

The present invention will find useful application in a variety of analytical systems that are designed for detection of an analyte present in one or more fluid streams. Gases are the preferred fluids according to the practice of the present invention, and therefore the following description of the invention will include a description of the arrangement, construction, and operation of a novel gas chromatographic analytical system (hereinafter, a chromatography.

For the purposes of the following description, the terms "fluid" and "pneumatic" will be considered to pertain to all types of fluids. "Fluid-handling function" refers to at least one of the following functions with respect to one or more fluid streams: initiation; distribution; and redirection; termination; control of temperature, pressure or flow rate; and sensing of temperature, pressure, or flow rate. "Fluid-handling functional device" refers to a device that provides one or more fluid-handling functions with respect to one or more fluid streams. "Electronic pneumatic control" and "EPC" refers to programmed electronic control of fluids and fluid handling functions, among which are included the control of volumetric flow rate and pressure of a fluid stream in a chromatograph, as for example in accordance with the invention disclosed by U.S. Pat. No. 4,994,096, and U.S. Pat. No. 5,108,466 in the names of Klein, et al., the disclosures of which are incorporated herein by reference, and to subsequent advances known in the art for programmed electronic pneumatic control of pressure, temperature, and/or flow rate of fluids in a chromatograph.

In a significant departure from the prior art, the present invention will be understood to overcome a major problem of chromatographic systems that employ a conventional carrier gas source, and also will be understood to provide improved detection of a wide range of analytes present in a fluid stream.

In the embodiments illustrated in the Figures and described below, like nomenclature and numerical identifiers refer to identical or equivalent structures; a single line indicates an electronic signal line capable of transmitting an electronic signal; double parallel lines indicate a pneumatic flow path capable of bearing a fluid stream; and dashed double parallel lines indicate an embedded pneumatic flow path in phantom.

Figure 1:
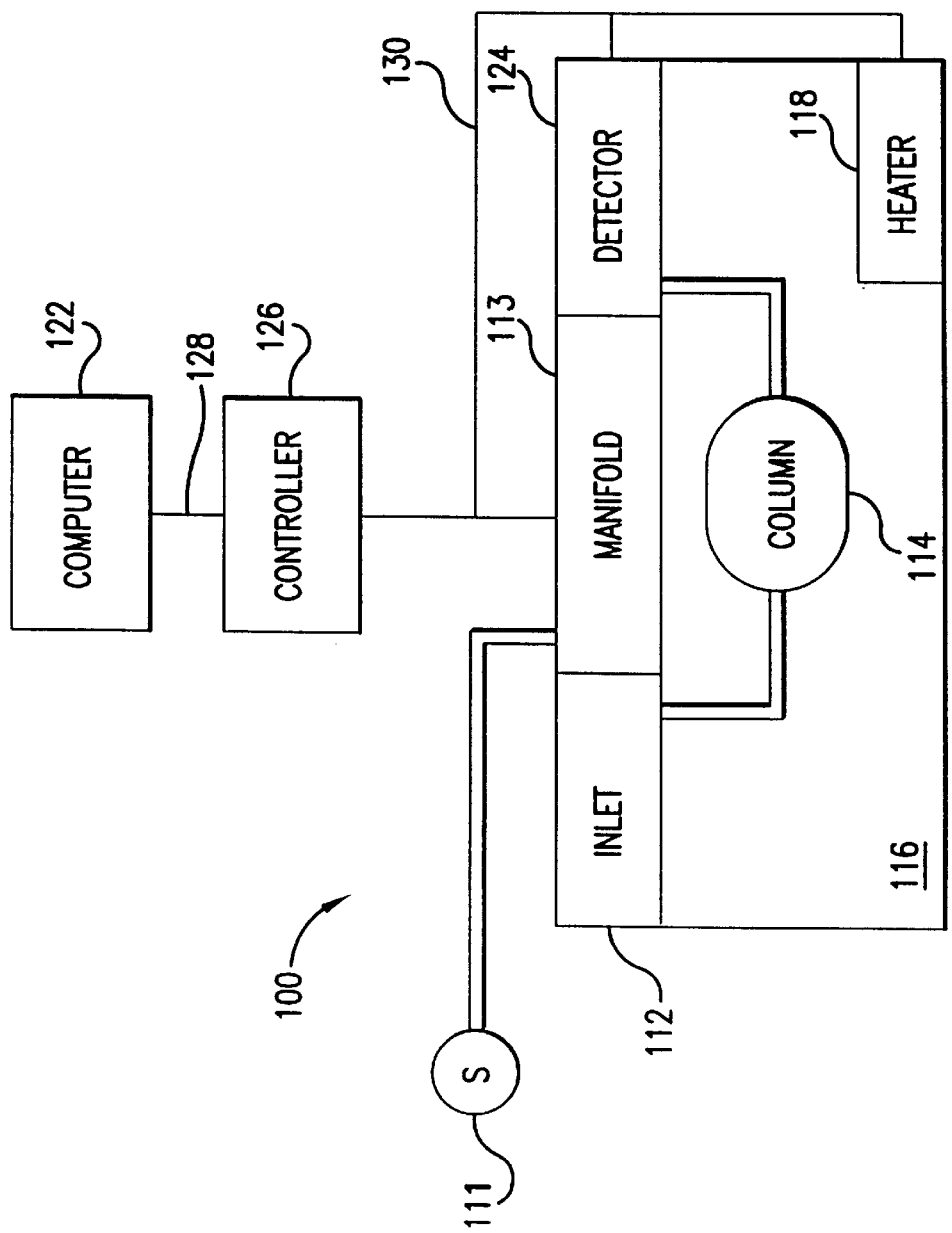
FIG. 1 is a simplified block diagram of an analytical instrument constructed as a chromatograph in accordance with the prior art.
Figure 2:
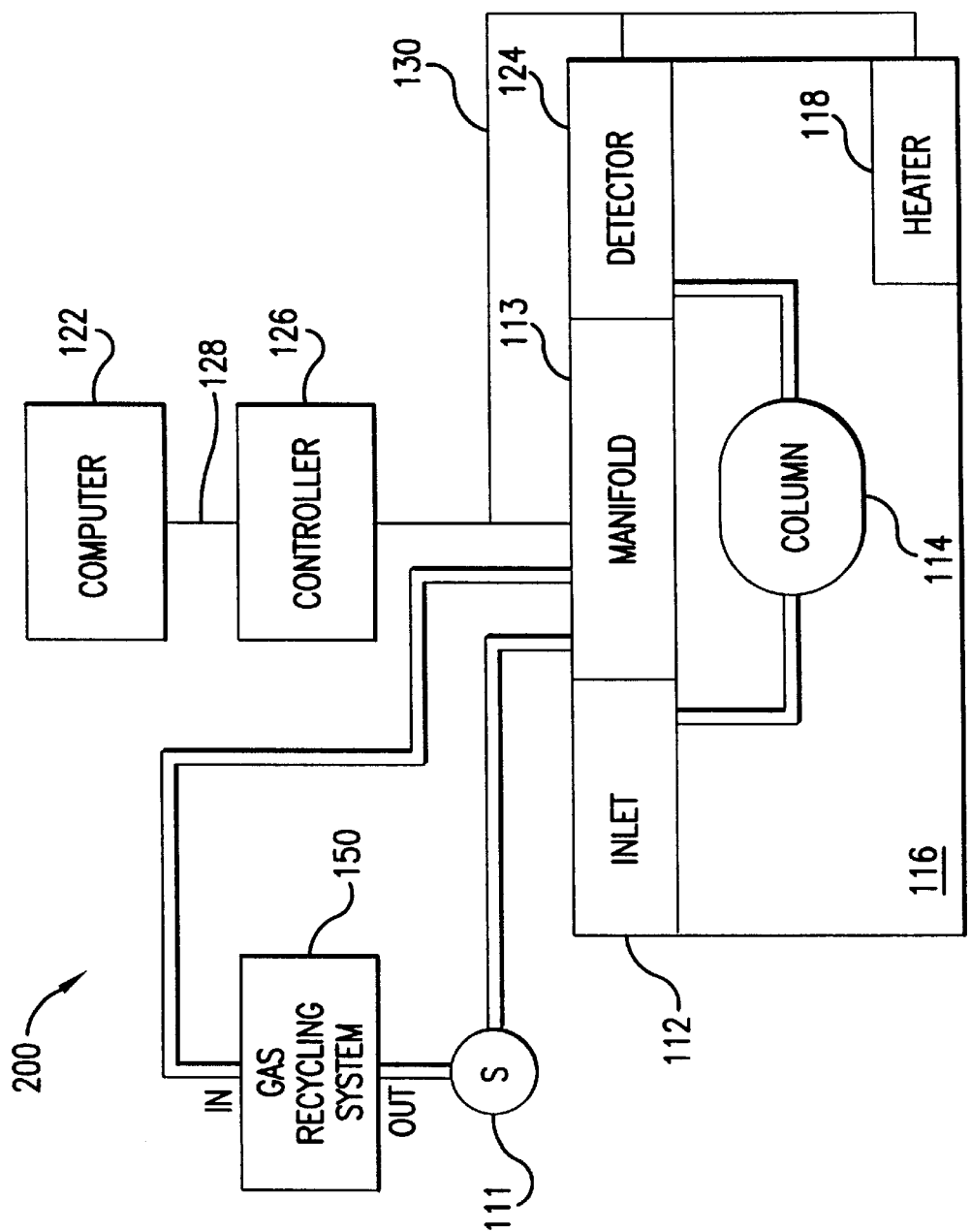
FIG. 2 is a simplified schematic view of first preferred embodiment of a chromatograph constructed according to the present invention.

A first preferred embodiment of an analytical instrument is shown in FIG. 2 and is generally designated as a chromatograph 200. In the illustrated embodiment, the manifold 113 is configured to include pneumatic pathways for receiving the combined gas flows that would otherwise be output from the detector 124 and the inlet 112 and vented to the atmosphere. Such combined gas flows are directed to a gas recycling system 150. The gas recycling system 150 then purifies and pressurizes the received gas flow to return a fluid stream of recycled gas to the source 111.

Figure 3:
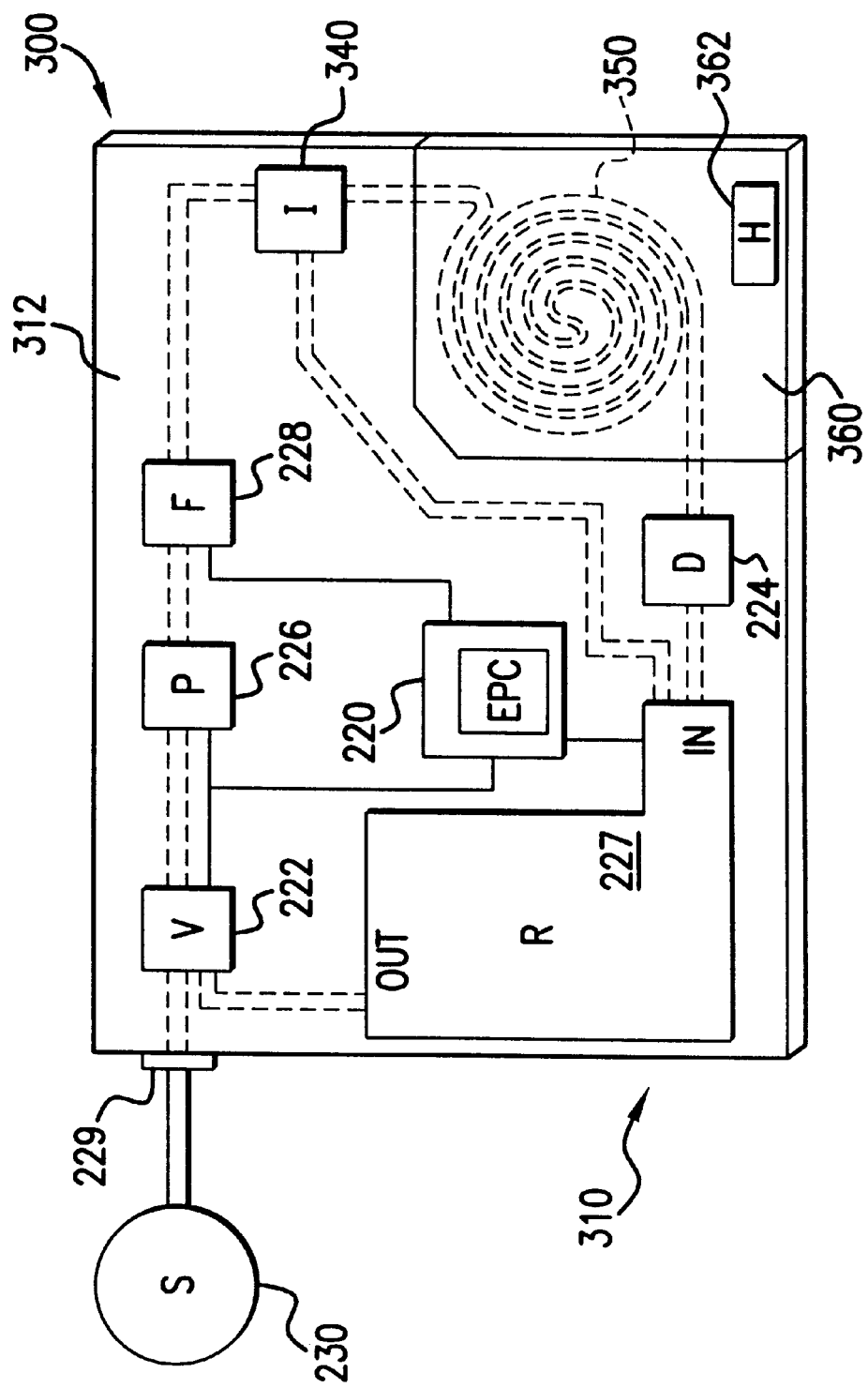
FIG. 3 is a simplified schematic view of second preferred embodiment of an analytical instrument constructed according to the present invention.

A second preferred embodiment of an analytical instrument is shown in FIG. 3 and is generally designated as a portable chromatograph 300. A sample is injected with a pressurized carrier fluid by means of an inlet 340. The carrier gas supplied to inlet 340 is initially provided from an outboard carrier gas source 230 connected to a pneumatic connector 229 into a planar manifold assembly 310, which serves in part to control and redirect a plurality of flows, including the carrier gas. The carrier gas and other fluid streams are directed to one or more fluid-handling functional devices such as valves, couplers, and the like in the planar manifold assembly 310 as will be described below. Certain fluid-handling functional devices, such as fittings, couplers, sensors, and the like in the planar manifold assembly 310 may be passive (such as a termination fitting) or active and hence operated under the control of a computer 220 and a pneumatic controller (EPC) by way of electronic pneumatic control signals provided on data and control lines. Hence, in a particular feature of the present invention, the pneumatic controller (EPC) effects electronic pneumatic control of, among other things, fluid flow rate, fluid pressure, fluid flow regulation, and the continuity or discontinuity of flow of one or more fluid flow streams in chromatograph 300 in part by the use of fluid-handling functional devices as will be described below. Accordingly, the computer 220, pneumatic controller (EPC), and fluid handling functional devices described herein may be operated to effect a variety of fluid-handling functions with respect to a wide range of fluid flow rates and pressures.

A separation column 350 is positioned within a controlled-temperature compartment 360. The sample/fluid mixture passing through column 350 is exposed to a temperature profile resulting in part from the operation of a heater 362 within the compartment 360. During its passage through the column 350, the sample will separate into its components primarily due to differences in the interaction of each component with the column 350 at a given temperature. As the separated components exit the column 350, they are detected by a detector 224. The detector 224 provides a detector output signal to controller (EPC) and computer 220 via respective data and control lines.

The computer 220 monitors the operation of the chromatograph 300 by signals from certain components, such as a pressure sensor 226, and flow sensor 228, and the detector 224, and initiates and maintains the fluid handling functions required for an analysis. Computer 220 maintains overall control of all systems associated with chromatograph 300. It will be recognized that any particular embodiment of chromatograph 300 may include more systems than those described in relation to the present invention. It will also be understood that although computer 220 and pneumatic controller (EPC) are shown as individual blocks, such computer 220 and pneumatic controller (EPC) may be integrated and may individually or jointly include a central processing unit and associated software, firmware, and peripheral devices, such as random access memories, read-only memories, input/output isolation devices, clocks, remote telemetry devices, and other related electronic components.

In a particular embodiment of the chromatograph 300, the separation column 350 is formed as a serpentine, etched-channel conduit provided within a planar manifold 312. One or both of the inlet 340 and separation column 350 may be installed in temperature-controlled compartment 360 which is temperature controlled by a suitable heater 362 according to a temperature sense signal provided to the computer 220 by an embedded temperature sensor (not shown).

The pressurized carrier gas output from the recycling system 227 is available to the valve 222 which is controlled by the electronic pressure control (EPC). Accordingly, the carrier gas required by the chromatograph 300 may be initially supplied by source 230. When a flow of recycled carrier gas becomes available from the output of the gas recycling system 227, the valve 222 may be operated to receive some or all of its carrier gas from the gas recycling system 227. In certain circumstances, the source 230 may be disconnected from the pneumatic connector 229 and the chromatograph 300 may be operated using carrier gas supplied by the gas recycling system 227.

A controlled stream of pressurized carrier gas passes through a pressure sensor 226 and a flow sensor 228, and then enters the inlet 340. In an embodiment wherein the inlet 340 is provided as a split/splitless inlet, the pressurized carrier gas is then divided into three streams. A first stream is directed to a septum purge line, a second stream is directed to a split line, and a third stream is directed to the column 350. The output of the septum purge line and the split line are combined at the Inlet 340 and directed to the gas recycling system 227. In the appropriate embodiments, a chemical trap is employed on the split line to prevent most of the sample material from reaching the split line such that the compounds capable of traversing the split trap are restricted to volatile compounds such as fixed gases.

Thus, and in accordance with another feature of the present invention, the planar manifold assembly 310 may be configured as a compact unit for portability, and the electronic pressure control can make use of advanced pressure control technology to control the flow of the recycled carrier gas stream.

The advantages of the above-described construction of the chromatograph 300 include the reduction of external connections between fluid-handling functional devices (such as fittings, valves, sensors, and the like) by use of a single planar manifold for the provision of a plurality of flow paths. The fluid-handling functional devices that connect to the planar manifold are preferably constructed to be surface-mounted, which has been found to offer reliable, fluid-tight connection without dead volume of conventional pneumatic connections. The number and complexity of external connections, which would otherwise undesirably increase the volume of the flow system, are also decreased.

A further advantage of the present invention is that multiple fluid-handling functional devices may be coordinated and assembled in a smaller volume than is possible in prior art systems. This results from the pneumatic channels that are integrated in the planar manifold, and thus many of the fluid flow paths are integral to the planar manifold. A large number of fluid-handling functional paths may be integrated into the planar manifold that heretofore would be difficult if not impossible to assemble using conventional techniques. Further details on the planar manifold assembly 310 contemplated by the present invention will be found with reference to a planar manifold assembly disclosed in commonly-assigned U.S. Pat. No. 5,567,868, entitled "Planar Manifold Assembly" and issued to Craig et al., and in U.S. application Ser. Nos. 08/846,607, 08/845,974, and 08/846,609, filed on Apr. 30, 1997 in the name of Stephen R. Craig, the disclosures of which are included herein by reference.

Preferably, the preferred embodiments of the gas recycling system 150, 227 each include first and second stages for effecting respective tasks of carrier gas purification and carrier gas pressurization.

The gas purification stage for each embodiment is designed according to the particular carrier gas operable in the particular embodiment of the chromatograph 200, 300. For example, in a hydrogen-based gas recycling system, the gas purification stage would preferably comprise a packed trap, such as molesieve, and a membrane or similar device permeable only by hydrogen, wherein the output stream of the packed trap is directed to, e.g., a palladium membrane that passes only pure hydrogen and its isotopes. In a helium-based gas recycling system, a similar packed trap may be employed and the output stream from the packed trap is then directed to a helium getter, a packed bed trap designed for cleaning helium, or a polymer barrier that is efficient for transmitting only helium. In still embodiments, that is, in a gas recycling system operable for recycling other carrier gases, a packed bed trap optimized for the particular carrier gas would be employed.

The pumping stage preferably employs a pumping system constructed in the form of a pumping mechanisms known in the art, such as a rotary pump or piston pump. Alternatively, in a hydrogen-based gas recycling system 227, the pumping system may be provided in the form of an electrochemical hydrogen pump.

Because the carrier gas is recycled, the chromatographs 200, 300 can operate for an extended period. For example, the only path by which carrier gas would be lost in chromatograph 300 would be by leaks present in the pneumatic pathways of the chromatograph.

Recycling of carrier gas is an advantage for the construction of: portable or hand-held chromatographs, remotely situated "online" chromatographs for environmental monitoring or process control, and bench top chromatographs for use in underdeveloped countries where a supply of conventional gas cylinders is unreliable or simply not feasible.

Although hydrogen permits the fastest chromatography, its use has heretofore been avoided because of the potential explosion hazard. Accordingly, because the carrier gas is conserved, the illustrated chromatographs 200, 300 may be constructed for safe operation with hydrogen carrier gas. That is, the hydrogen gas may be maintained in a closed loop such that much of the hazard presented by the use of hydrogen gas is contained. This would permit the chromatographs 200, 300 to be placed in an adverse environment without compromising most safety requirements.

Furthermore, the recycling of the carrier gas in the chromatographs 200, 300 minimizes the chances for contamination of the carrier gas stream. The analytical performance of the illustrated chromatographs is accordingly enhanced.

While the invention has been described and illustrated with reference to specific embodiments, those skilled in the art will recognize that modification and variations may be made without departing from the principles of the invention and set forth in the following claims.

What is claimed is:

1. A chromatograph for analysis of an analyte, comprising:

an inlet for receiving a carrier fluid stream and a sample containing the analyte, and in response, providing a sample/fluid mixture;

a separation column connected to the inlet for receiving the sample/fluid mixture and for providing a column effluent stream;

a detector for receiving the column effluent stream and for providing a detector output stream, whereby the detector provides a detector signal representative of a characteristic of the analyte; and a gas recycling system for a) receiving a received gas stream provided in the form of the detector output stream and a portion of the carrier fluid stream not present in the sample/fluid mixture, b) purifying the received gas stream to provide a purified gas stream, and c) pressurizing the purified gas stream so as to provide a recycled carrier gas stream, such that the recycled carrier gas stream may be made available for operating the chromatograph.

2. The chromatograph of claim 1, further comprising:

a sensor for sensing a volumetric flow rate of the sample/fluid mixture entering the separation column and for generating a respective flow rate signal; and a pneumatic controller for receiving the flow rate signal and for controlling in response a volumetric flow rate of the carrier fluid.

3. The chromatograph of claim 1, further comprising an electronic pressure controllers and wherein the recycled carrier gas stream is subject to control by the electronic pressure controller, whereby unwanted flow rate variation in the recycled carrier gas stream subject to detection is reduced.

4. The chromatograph of claim 1, wherein the gas recycling system further comprises a first stage in the form of a gas purification system and a second stage in the form of a gas pressurization system.

5. The chromatograph of claim 4, wherein the carrier gas is hydrogen and the gas recycling system is a hydrogen-based gas recycling system.

6. The chromatograph of claim 5, wherein the gas purification system comprises a packed trap and a device permeable only by hydrogen.

7. The chromatograph of claim 4, wherein the carrier gas is helium and the gas recycling system is a helium-based gas recycling system.

8. The chromatograph of claim 7, wherein the gas purification system comprises a device selected from the group consisting of: a helium getter, a packed bed trap designed for cleaning helium, and a polymer barrier that is efficient for transmitting only helium.

9. A chromatograph for analysis of an analyte comprising:

an inlet for receiving a carrier fluid stream and a sample containing the analyte, and in response, providing a sample/fluid mixture;

a separation column connected to the inlet for receiving the sample/fluid mixture and for providing a column effluent stream;

a detector for receiving the effluent stream and for providing a detector output stream, whereby the detector provides a detector signal representative of a characteristic of the analyte;

a gas recycling system for a) receiving a received gas stream provided in the form of the detector output stream and a portion of the carrier fluid stream not present in the sample/fluid mixture, b) purifying the received gas stream to provide a purified gas stream, and c) pressurizing the purified gas stream so as to provide a recycled carrier gas stream; and a planar manifold assembly having a planar manifold operably connected to a selected one of the inlet, separation column, detector, and gas recycling system, the planar manifold assembly having a plurality of channels embedded therein, and wherein a selected one of the inlet, separation column, detector, and gas recycling system is mounted on the planar manifold assembly and pneumatically connected to at least one of the channels, whereby the recycled carrier gas stream may be made available for operating the chromatograph.

10. The chromatograph of claim 9, wherein the planar manifold assembly comprises a serpentine channel adapted for operation as the separation column.

11. The chromatograph of claim 9, further comprising:

a sensor for sensing a volumetric flow rate of the sample/fluid mixture entering the separation column and for generating a respective flow rate signal; and a pneumatic controller for receiving the flow rate signal and for controlling in response a volumetric flow rate of the carrier fluid.

12. The chromatograph of claim 9, further comprising:

an electronic pressure controller, and wherein the recycled carrier gas stream is subject to control by the electronic pressure controller, whereby unwanted flow rate variation in the recycled carrier gas stream subject to detection is reduced.

* * * * *